(12) United States Patent
Egger (10) Patent No.: US 7,384,379 B2
(45) Date of Patent: Jun. 10, 2008

(54) FITNESS DEVICE

(76) Inventor: Norbert Egger, Eschenbachgasse 4 A, 5020 Salzburg (AT)

( * ) Notice: Subject to any disclaimer, the term of this patent is extended or adjusted under 35 U.S.C. 154(b) by 255 days.

(21) Appl. No.: 10/490,571

(22) PCT Filed: Oct. 1, 2002

(86) PCT No.: PCT/EP02/10980

§ 371 (c)(1), (2), (4) Date: May 27, 2004

(87) PCT Pub. No.: WO03/030808

PCT Pub. Date: Apr. 17, 2003

(65) Prior Publication Data

US 2005/0070405 A1  Mar. 31, 2005

(30) Foreign Application Priority Data

Oct. 2, 2001  (DE) .............................. 101 49 418

(51) Int. Cl.
*A63B 26/00* (2006.01)
(52) U.S. Cl. ..................... 482/78; 482/139; 482/148
(58) Field of Classification Search ............... 482/148, 482/78, 139, 105, 69; D2/728, 731; 434/395; 441/188, 88; 450/110; 2/311, 69; 601/151; 128/293, 24 R, 200.24; 33/2 R
See application file for complete search history.

(56) References Cited

U.S. PATENT DOCUMENTS

| | | | | |
|---|---|---|---|---|
| 726,791 A | * | 4/1903 | Armbruster | .................. 601/11 |
| 1,440,157 A | * | 12/1922 | Lawton | ....................... 604/312 |
| 3,859,989 A | * | 1/1975 | Spielberg | ....................... 601/11 |
| 4,030,488 A | * | 6/1977 | Hasty | ........................... 601/152 |
| 4,230,114 A | * | 10/1980 | Feather | ........................ 604/312 |
| 4,374,518 A | * | 2/1983 | Villanueva | ................... 601/152 |
| 4,421,109 A | * | 12/1983 | Thornton | ...................... 601/35 |
| 4,738,249 A | * | 4/1988 | Linman et al. | .............. 601/152 |
| 4,836,192 A | * | 6/1989 | Abbate | .......................... 601/7 |
| 4,876,746 A | * | 10/1989 | Howie | ............................. 2/69 |
| 5,222,478 A | * | 6/1993 | Scarberry et al. | .............. 601/44 |
| 5,383,894 A | * | 1/1995 | Dye | ............................ 606/201 |
| 5,458,562 A | * | 10/1995 | Cooper | ........................ 601/151 |

FOREIGN PATENT DOCUMENTS

| | | |
|---|---|---|
| AT | 400 305 B1 | 12/1995 |
| DE | 843 887 C1 | 7/1952 |
| DE | 28 29 082 A1 | 1/1980 |
| FR | 2 789 893 A1 | 8/2000 |
| NO | 318684 | 12/2000 |
| WO | WO-01/52787 A2 | 7/2001 |

* cited by examiner

*Primary Examiner*—Lori Amerson
(74) *Attorney, Agent, or Firm*—Darby & Darby PC (57) ABSTRACT

The present invention relates to a fitness device (1) in the form of a garment, comprising at least one skin stimulation means (5) which is actuated by fluid pressure and, in a stimulation area (13, 16), acts on the skin surface of a wearer (2) of the fitness device. Such fitness devices are known as low pressure suits. To enhance the action of said fitness devices, the skin stimulation means (5) is transferred according to the invention from a low pressure state, in which a low pressure acts on the skin surface (19) in the stimulation area (20), into an overpressure state, in which an overpressure acts on the skin surface (19) in the stimulation area (18).

17 Claims, 6 Drawing Sheets

FITNESS DEVICE

The present invention relates to a fitness device in the form of a garment, comprising at least one skin stimulation means which acts in a stimulation area on the skin surface of a wearer of the fitness device and has a plurality of pressure chambers by which in a negative pressure state in the stimulation area a negative pressure acting on the skin surface can be produced, and which is designed to be transferred from the negative pressure state into an overpressure state, during overpressure acts which in the stimulation area on the skin surface.

It has already been known for more than 5000 years that the action of a negative pressure on the skin surface is conducive to health. In ancient times cow horns were used with a hole for sucking off air and for collecting tissue fluid in the stimulation area by the action of negative pressure. Later, instead of cow horns, cupping glasses were used that were filled with hot air. Upon cooling the air contracted, thereby forming a negative pressure.

In modern times these methods have been developed further and partly been used commercially.

U.S. Pat. No. 726,791, for instance, discloses a negative pressure suit which comprises rigid spacers. The drawback of this suit is, however, the absence of any freedom of movement because of the rigid spacers by which the cover of the suit is kept spaced apart from the skin surface. Moreover, in the case of the suit of U.S. Pat. No. 726,791, a selective action up on specific body areas is not possible.

U.S. Pat. No. 1,440,157 shows a belt-like fitness device that forms a negative pressure zone in the abdominal region. In this device, negative pressure is produced by the elastic forces of a forwardly bulging membrane.

U.S. Pat. No. 4,230,114 shows fitness pants in which a negative pressure is produced. To distribute the negative pressure approximately evenly in the fitness pants, fixed spacers are provided in the area of the suction lines.

The devices of U.S. Pat. No. 1,440,157 and U.S. Pat. No. 4,230,114 do not allow for a selective adaptation of the negative pressure area to specific body zones.

Finally, WO 01/52787, which originates from the applicant, describes a fitness device in the form of a garment, which in a negative pressure chamber that is delimited at one side by the body of the wearer of the garment, a negative pressure is produced that acts on the skin surface. To prevent the cover of the fitness device from resting on the body, spacers are provided that can be inflated. To adapt the body areas acted upon by negative pressure to individual body sections, a plurality of negative-pressure chambers can also be provided in the fitness device of WO 01/52787.

Although the device of WO 01/52787 already achieves a very strong fitness-promoting effect, said effect can still be enhanced.

Starting from WO 01/52787, it is therefore the object of the present invention to enhance the fitness-promoting effect of a fitness device having the aforementioned features.

Said object is achieved for the generic fitness device in that the pressure chamber is designed as a hollow chamber which during the negative pressure state is acted upon with a chamber pressure below the ambient pressure.

This solution according to the invention enhances the fitness-increasing effect of the fitness device over conventional devices. First of all, as has so far been the case, tissue fluid with blood and lymph fluid is sucked in the negative pressure state into the subcutaneous fatty tissue of the stimulation area. This increases metabolism and cell activity in the stimulation area.

By switching into the overpressure state, the tissue fluid is pressed out of the stimulation area by overpressure. The massage effect of the device created thereby increases the blood circulation-enhancing effect and thus the effect of the device in comparison with the devices known from the prior art.

The terms "overpressure" and "negative pressure" refer to a pressure higher or lower than ambient pressure.

The fitness-enhancing effect of the inventive fitness device can be improved in an advantageous variant in that a plurality of skin stimulation means are provided that are connected to the control means and can be transferred independently of one another from the negative pressure state into the overpressure state. This design permits an adaptation of the stimulated skin area to the body characteristics of the wearer of the fitness device because of an independent control or actuation of the skin stimulation means. In this variant, specific problem zones can thus be acted upon in a selective way.

In a further development, individual ones of the plurality of skin stimulation means are coupled such that they always react to the switching signal simultaneously.

In a particularly advantageous variant, the control means may comprise a controller by which the sequence of the switching signals to individual skin stimulation means can be adjusted. The sequence of the switching operations from the negative pressure state into the overpressure state, and vice versa, can thereby be coordinated. This design makes it possible that e.g. the stimulation area subjected to overpressure can be controlled by selective actuation of the skin stimulation means and by a selective sequence of the switching signals to the individual skin stimulation means along specific paths over the skin surface. This leads to a selective massage effect that is adapted to the anatomical conditions of the human body. For instance, the overpressure area can be controlled in the direction of the bloodstream towards or away from the heart, or the stimulation area can only be moved above specific muscles.

The skin stimulation means may particularly comprise a pressure chamber that is acted upon in the overpressure state with a chamber pressure greater than the ambient pressure, and/or is acted upon in the negative pressure state with a chamber pressure lower than the ambient pressure. Such pressure chambers can be controlled easily by way of vacuum pumps and valve control.

The pressure chambers may be designed as hollow chambers that depending on the switching signal are connectable to the suction side and/or the pressure side and/or an outlet of a fluid pump connected to the environment. Depending on which outlet of the pump the pressure chamber is connected to, it is acted upon with negative pressure or overpressure.

In particular, the skin stimulation means may be supported on the skin surface in the overpressure state. In this configuration, the skin stimulation means serves as a spacer in the overpressure state. In a further advantageous configuration, the skin stimulation means may be spaced apart from the skin surface in the negative pressure state.

In a further configuration, the hollow chamber may have a flexible cover at least in sections, so that it expands in the overpressure state and contracts in the negative pressure state.

In another advantageous variant, the skin stimulation means may also comprise an elastic element by which in the overpressure state pressure is exerted on the stimulation area. The elastic element may e.g. be in the form of resilient clasps that stretch the pressure chamber or in the form of springs that are supported on the skin surface of the wearer of the fitness device. When in this variant the skin stimulation means is acted upon by a negative pressure, said negative pressure acts against the pressure of the elastic elements and compresses said elements. Due to the elastic elements, the generation of an overpressure in the overpressure state can be dispensed with, which considerably simplifies the construction of the fitness device.

Instead of the operation of the skin stimulation means by fluid pressure, a mechanical operation may be provided. To this end, a further variant provides for an element by which in the overpressure state pressure is exerted on the stimulation area. This element may e.g. be designed in the manner of a belt and may surround the wearer's body at least partially. Pressure is here exerted by reducing the circumference.

The fitness device may further be equipped with a magnetic field device by which a magnetic field acting on the body of the wearer of the fitness device can be produced. With said magnetic field, positive effects can be achieved in the body of the wearer of the fitness device.

Moreover, according to a further advantageous variant, there may also be provided a radiation means by which the wearer's body is irradiated at least partially with light in the visible range or in the infrared or ultraviolet range. With the help of optical waveguides, e.g. glass fiber cables, light can be guided in an advantageous variant from a light source to specific areas of the wearer. This permits greater degrees of freedom in the design of the fitness device because the light source can be mounted at any desired place. A local heating of the skin can be achieved by irradiating the skin surface with infrared rays. The hormone balance in the skin surface can be influenced by specific wavelengths of light beams.

To maintain a climate within the fitness device conducive to the respective application, a climate control means may be provided in an advantageous configuration for controlling the moisture and/or temperature at least partially in the area of the fitness device adjoining the skin surface. This control may be performed by e.g. controlling the moisture of the fluid introduced into the fitness device or the temperature thereof. In an inexpensive variant of the fitness device, ambient air is particularly suited as the fluid. However, it is also possible to use other gases, such as noble gases or gas mixtures, which have a fitness-promoting effect upon skin contact.

To give the wearer of the fitness device more freedom of movement and to enable him/her at the same time to perform physical exercise during operation of the fitness device, for instance in a fitness studio, the fitness device, which is designed as a garment, is made flexible to follow movements, so that it can follow the movements of its wearer without any great impediment. To this end, the fitness device may particularly comprise a flexible cover that is preferably fluid-impermeable in the stimulation area. The fitness device particularly serves as a protective suit during simultaneous physical exercise. The wearing comfort is once again increased by a corresponding internal lining which imparts a pleasant wear feeling, for instance a nonwoven material.

Furthermore, the invention relates to a slimming method by means of a fitness device designed as a garment, comprising at least one fluid pressure-actuated skin stimulation means which acts on a stimulation area of the skin surface of the wearer of the fitness device.

For enhancing the fitness-promoting and slimming effect of the fitness device, the skin simulation means according to the invention alternately exerts a negative pressure and an overpressure on the stimulation area.

The fitness device may be designed in the form of pants, in the form of a shirt, in the form of a whole-body suit or in the form of arm or leg bandages or abdominal bandages.

The fitness device according to the invention will now be explained in more detail with reference to embodiments taken in conjunction with the attached figures. Like reference numerals are here used for like components.

First of all, the construction of a first embodiment of the fitness device according to the invention will be described with reference to FIG. 1.

Figure 1:
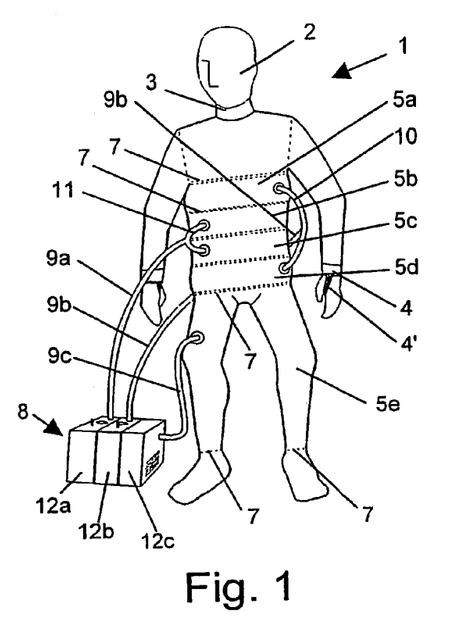
FIG. 1 shows a first embodiment of a fitness device according to the invention.

FIG. 1 shows a fitness device 1 in the form of a garment worn by a wearer 2, who is just shown schematically. The fitness device 1 has the form of a whole-body suit or overall which is provided with a collar 3 and cuffs 4 on the arms. The cuffs 4 seal the interior of the fitness suit 1. Thumb loops 4' prevent the suit from slipping.

The fitness suit 1 is provided with skin stimulation means 5a-d of a substantially tubular configuration extending over the whole girth of wearer 2. When reference is made in the following in a merely generic way to the skin stimulation means, the letters will be omitted. In the area of the legs, a further skin stimulation means 5e is provided.

The area of each skin stimulation means 5 defines a stimulation area on the skin surface of wearer 2 in which the skin stimulation means acts on the body of the wearer 2 by means of a negative pressure or overpressure. The skin stimulation areas 5a-d are separated from one another by separating portions 7. The separating portions 7 isolate the stimulation areas from one another such that a skin stimulation means 5 only acts on the stimulation area assigned to it.

In the embodiment of FIG. 1, a total of four skin stimulation means 5a-d are provided in the trunk portion. The skin stimulation means 5e, which is arranged on the legs, acts on both legs at the same time. The number of the skin stimulation means 5 can be varied, depending on need and on the size of the suit.

The skin stimulation means of FIG. 1 are actuated by fluid pressure generated by a pump device 8. A gas, for instance an inert gas such as helium or carbon dioxide, or a mixture of gases, e.g. ambient air, is used as the fluid in the embodiment of FIG. 1. For specific applications, however, liquids may also be used as the fluids.

The fluid pressure generated by the pump device 8, i.e. a pressure which is lower or higher than the ambient pressure prevailing in the environment outside the fitness device, is passed on via pressure feed lines 9a, 9b, 9c to the skin stimulation means. To this end, the pressure feed lines 9a, 9b, 9c are connectable to the suction side or pressure side of the pump device 8.

As can be seen in FIG. 1, the uppermost and lowermost skin stimulation means 5a and 5d are coupled in the trunk area by a connection line 10 in the embodiment of FIG. 1. The connection line 10 is connected to the pressure feed line 9b, so that the uppermost and the lowermost skin stimulation means 5 in the trunk area have the same fluid pressure at all times.

Likewise, the two central skin stimulation means 5b and 5c are interconnected in the trunk area via a connection line 11. The connection line 11 is connected to the pressure feed line 9a, so that the same fluid pressure always prevails in the two skin stimulation means 5b and 5c. The skin stimulation means 5e on the legs is acted upon separately with fluid pressure via a pressure feed line 9c, as can be seen in FIG. 1.

In the pump device 8, there is a control means (not shown) that outputs a switch signal upon which, via switch valves 10a-c, the pressure feed lines 9a-c are acted upon either with overpressure or with negative pressure. Hence, each skin stimulation means 5 in the stimulation area assigned to it can apply either a negative pressure or an overpressure to the skin surface.

When a negative pressure acts on the skin surface, blood and tissue fluid is collected in the stimulation area. In the overpressure state, blood and tissue fluid are pressed out of the stimulation area.

The fitness device in the form of a suit in FIG. 1 is operated as follows: First of all, air is sucked out of the suit via pressure line 9c, so that a negative pressure between 50 and 600 millibar prevails in the fitness device. The air-tight outer skin of the suit presses with a corresponding pressure onto the skin of person 2, who is inside suit 1. The pressure line 9a is connected to the suction side of the pump device 8 whereas pressure line 9b is connected to the pressure side of the pump. The skin stimulation means 5a and 5d are thus inflated, so that the skin stimulation means 5b and 5c which are positioned between said skin stimulation means and acted upon with a negative pressure are lifted from the person's skin. Overpressure prevails underneath the inflated air chambers whereas a negative pressure acts on the skin underneath the evacuated air chambers.

For enhancing the effect, in the embodiment of FIG. 1 and also in the following embodiments, there may be provided devices for generating a magnetic field, light sources with glass fiber lines, and climate control means for controlling the air conveyed by the pump device 8.

Figure 2:
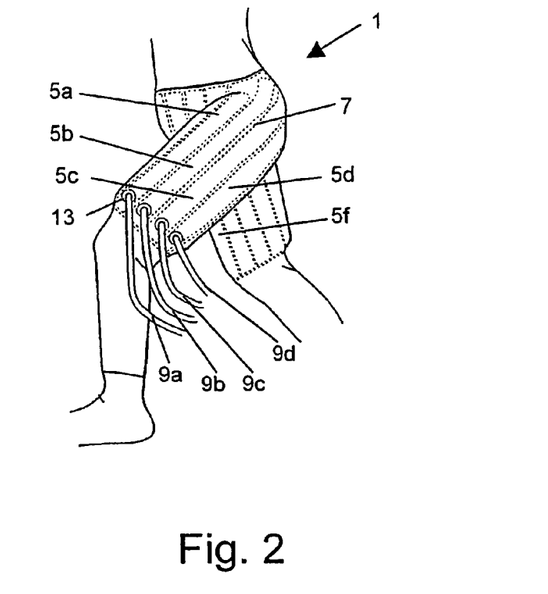
FIG. 2 shows a second embodiment of a fitness device according to the invention.

FIG. 2 shows a second embodiment of a fitness device according to the invention that is designed in the form of pants and flexible so that it permits normal physical exercise of the wearer. The stimulation areas extend in this embodiment over the thigh portion, lower abdomen portion and bottom portion, so that the embodiment of FIG. 2 is particularly suited for reducing fat in the thigh portion, bottom portion and lower abdomen portion. The skin stimulation means 5 assigned to the stimulation areas extend in the direction of the leg length from shortly above the knee up to the waist. Each skin stimulation means is separated by a separating portion 7 from the neighboring skin stimulation means and provided with a connection 13 which has connected thereto a pressure feed line 9. Each pressure feed line 9 is actuable separately and independently of the pressure feed line 9 of another skin stimulation means 5 by fluid pressure—negative pressure or overpressure. For the sake of simplicity, only four pressure lines 9a-d are shown in FIG. 2 and assigned to the skin stimulation means 5a-d; the remaining pressure feed lines have been omitted.

Furthermore, in the embodiment of FIG. 2, there is provided a climate control means (not shown) by which temperature and/or moisture in the fitness pants 1 can be regulated to adjustable values. This is e.g. done by controlling the compressed air supplied through the pressure feed lines.

Figure 3A:
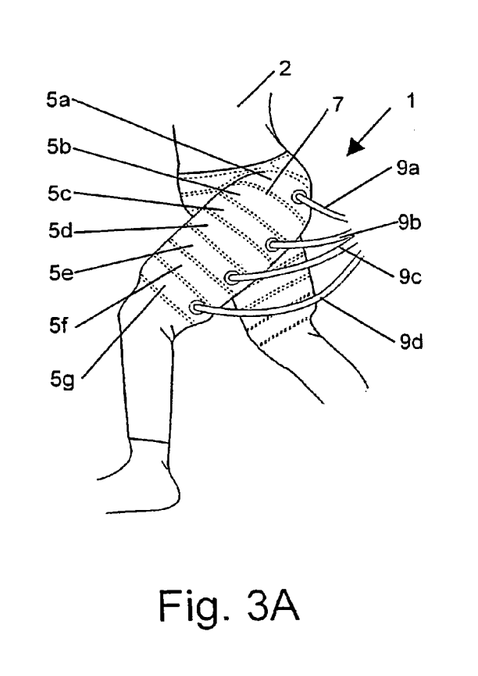
FIG. 3A shows a third embodiment of a fitness device according to the invention.
Figure 3B:
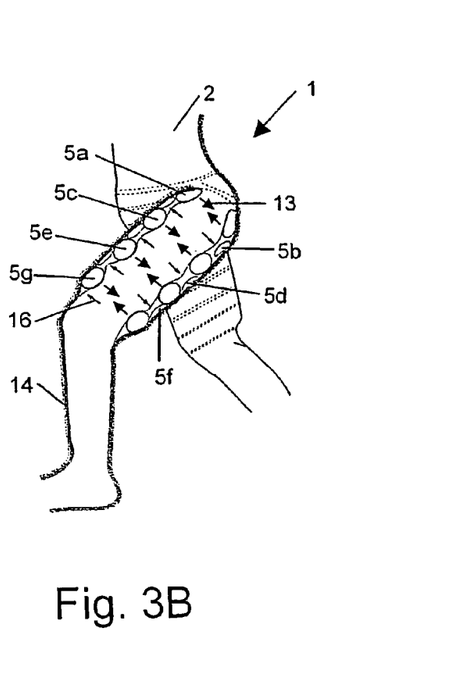
FIG. 3B shows the embodiment of FIG. 3A in cross section.

FIG. 3A shows a third embodiment that is also designed as a pair of pants. FIG. 3B shows the third embodiment in cross section. In contrast to the embodiment of FIG. 2, the stimulation areas extend in the embodiment of FIG. 3 with the associated skin stimulation means in circumferential direction around the thighs and waist. For the sake of simplicity, only every second skin simulation means is shown with a pressure feed line in the embodiment of FIG. 3A.

As can be seen in the cross section of FIG. 3B, the hollow chamber-like skin stimulation means 5a, 5c, 5e and 5g are inflated by being acted upon with overpressure. As a result, the skin stimulation means 5a, 5c, 5e and 5g are supported on the skin, exerting a pressure thereon. Hence, stimulation areas 13 that are subjected to overpressure are formed, which are schematically illustrated in FIG. 3B by the arrows directed towards the body. A negative pressure prevails in the intermediate hollow chamber-like skin stimulation means 5b, 5d and 5e, so that said means collapse. Since the cover of the skin stimulation means is flexible, the covers are contracted in the skin stimulation means 5b, 5d and 5e subjected to a negative pressure. Since the skin stimulation means 5b, 5d, 5e which are subjected to negative pressure are provided on the cover 14 of the fitness device 1 and are pressed away by the inflated skin stimulation means from the body of wearer 2, a hollow chamber 15 is respectively formed between the skin stimulation means 5b, 5d and 5e subjected to the negative pressure, the hollow chamber exerting a suction effect on the skin surface positioned thereunder. This suction effect forms negative-pressure stimulation areas 16 which are shown in FIG. 3B by the arrows directed out of the body of wearer 2. In dependence upon the geometrical design of the skin stimulation means 5, the stimulation area can be adapted to individual muscle forms. Moreover, any desired patterns can be composed with the help of the skin stimulation means, said patterns permitting any desired cooperation and any desired adaptation of the stimulation areas to the body geometry. This is shown by way of example in FIG. 4.

Figure 4:
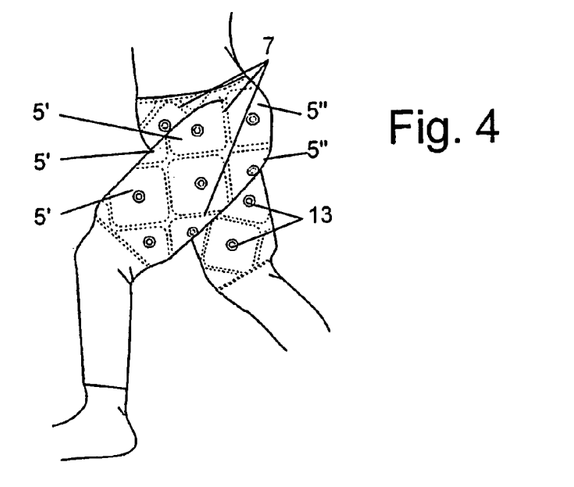
FIG. 4 shows a fourth embodiment of a fitness device according to the invention.

In the embodiment of FIG. 4, the stimulation areas are approximately rectangular. However, they may also be polygonal, round or rounded. Each skin stimulation means 5 is provided with a flexible tube connection 13 and can be actuated independently. When several skin stimulation means are acted upon in parallel by the same pressure, they cooperate with one another, thereby forming a coherent stimulation area. For instance, in the embodiment of FIG. 4, the skin stimulation means 5' are operated together such that the stimulation area only extends over the four-headed thigh muscle. Irrespective of this, the skin stimulation means 5" can be actuated jointly, so that a further stimulation area only extends over the buttocks muscle.

Figure 5A:
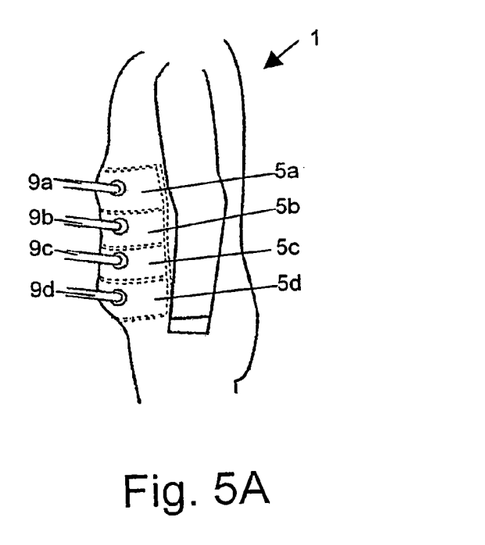
FIG. 5A shows a fifth embodiment of a fitness device according to the invention.
Figure 5B:
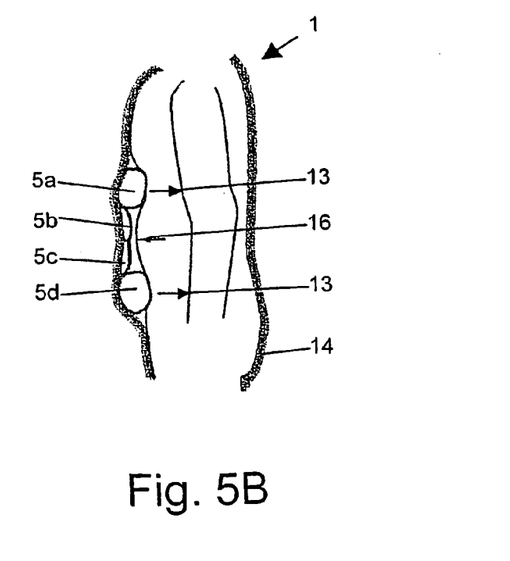
FIG. 5B shows a cross section through the embodiment of FIG. 5A.

FIG. 5A shows a fifth embodiment of the fitness device according to the invention, FIG. 5B a cross section through said embodiment. In the embodiment of FIG. 5A, four skin stimulation means 5a-d are shown in the abdominal region of the fitness suit 1.

As can be seen in the cross section of FIG. 5B, the skin stimulation means are formed by hollow chambers whose cover 16 is flexible. The flexible cover 16 of the fitness suit can also be seen in this illustration. For sweat absorption the flexible cover 16 is lined on the inside with a soft comfortable nonwoven material.

In the illustration of FIGS. 5A and 5B, the uppermost skin stimulation means 5a and the lowermost skin stimulation means 5d are acted upon by overpressure, so that they are in the inflated overpressure state. The two central skin stimulation means 5b and 5c are acted upon by a negative pressure, so that they are contracted in the negative pressure state. In the overpressure state, the skin stimulation means 5a and d are supported in the stimulation areas 13 on the skin surface 19 of the wearer 2 and exert an overpressure on the tissue positioned thereunder.

In the stimulation area 16, which is assigned to the two skin stimulation means 5b and c in the negative pressure state, a negative pressure is prevailing.

The two inflated skin stimulation means 5a and 5d serve as spacers, so that the two collapsed skin stimulation means 5 are pressed away from the skin surface 19 of the wearer 2. As a result, a chamber 15 which is acted upon by negative pressure is formed between the skin stimulation means 5 in the negative pressure state and the skin surface 19.

When the two central skin stimulation means 5b, c are now acted upon by an overpressure, and the two skin stimulation means 5a, d located at the periphery are acted upon by a negative pressure, the two skin stimulation means 5a, d located at the periphery will collapse and form thereunder a respective chamber 15 with a negative-pressure stimulation area 16 whereas the two central stimulation means press onto the skin and form an overpressure stimulation area 13.

Figure 6A:
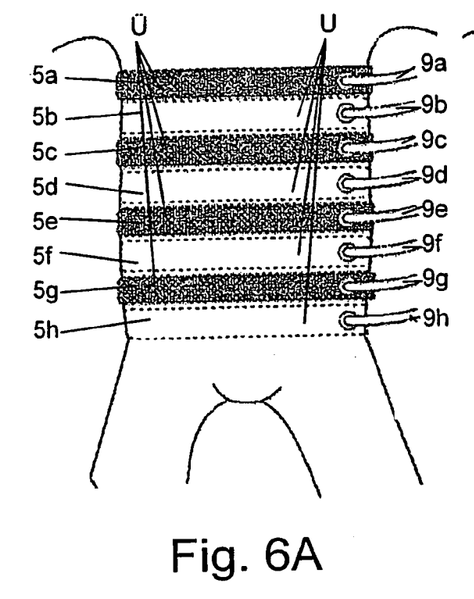
FIG. 6A shows a sixth embodiment of the fitness device according to the invention, in a first operative state.
Figure 6B:
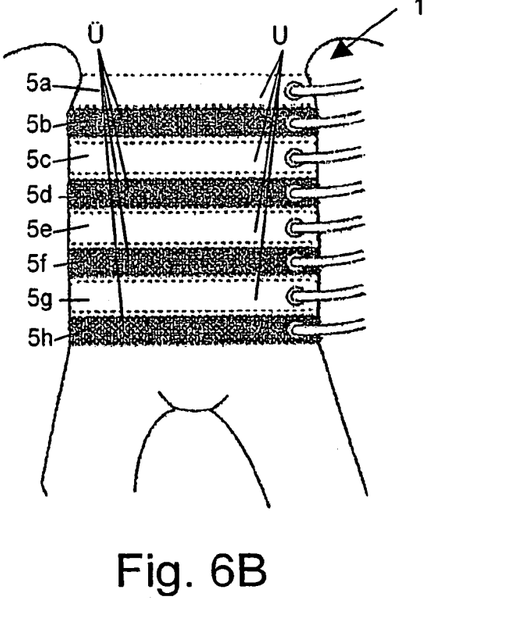
FIG. 6B shows the embodiment of FIG. 6A in a second operative state.

FIGS. 6A to 6D show a first mode of operation of a further embodiment of a fitness device 1 according to the invention in the form of a garment. The skin stimulation means that are acted upon by negative pressure are designated by U in FIGS. 6A to 6D and the ones acted upon by overpressure by Ü. These correspond to negative-pressure and overpressure stimulation areas 13 and 16, respectively. In FIGS. 6A and 6B, the skin stimulation means acted upon by overpressure are shown in a dark shade.

The fitness device of FIGS. 6A to 6D is designed in the form of an abdominal bandage which extends from the hip area up to below the armpits. The fitness device comprises a total of eight concentric ring-like skin stimulations means 5a-h in the trunk area, with pressure feed lines 9a-h being assigned to them. The skin stimulation means are acted upon via the pressure feed lines 9a-b with a negative fluid pressure or a fluid overpressure. Every second skin stimulation means is here connected in parallel to the same source of pressure.

In the initial position shown in FIG. 6A, starting with the first skin stimulation means 5a, every second skin stimulation means 5a, 5c, 5e, 5g is acted upon by overpressure whereas, starting with the second skin stimulation means 5b, every second skin stimulation means 5b, 5d, 5f, 5h is acted upon with negative pressure. At regular time intervals, for instance every 5 to 40 seconds, preferably every 10 to 20 seconds, the first operative state shown in FIG. 6A is switched over to the second operative state shown in FIG. 6B. In the operative state of FIG. 6B, starting with the uppermost skin stimulation means 5a, every second skin stimulation means 5a, 5c, 5e, 5g is now acted upon by negative pressure whereas, starting with the second skin stimulation means 5b from above, every second skin stimulation means 5b, 5d, 5f, 5h is now acted upon by overpressure. The overpressure in the inflated chambers is here 10 to 50 or 200 to 800 millibar; the pressure difference between overpressure and negative pressure is preferably 20 to 10 millibar.

Figure 6C:
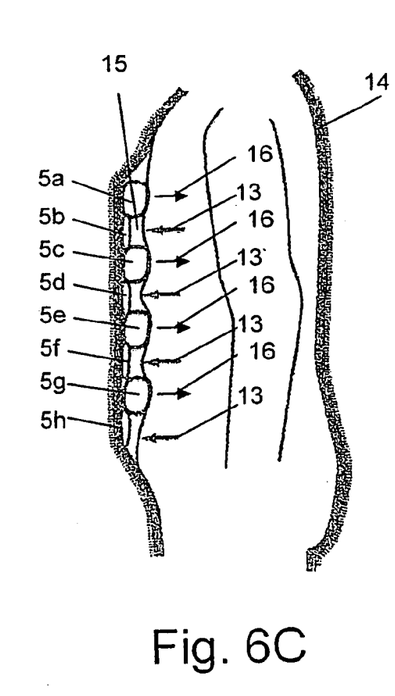
FIG. 6C shows a cross section through FIG. 6A.
Figure 6D:
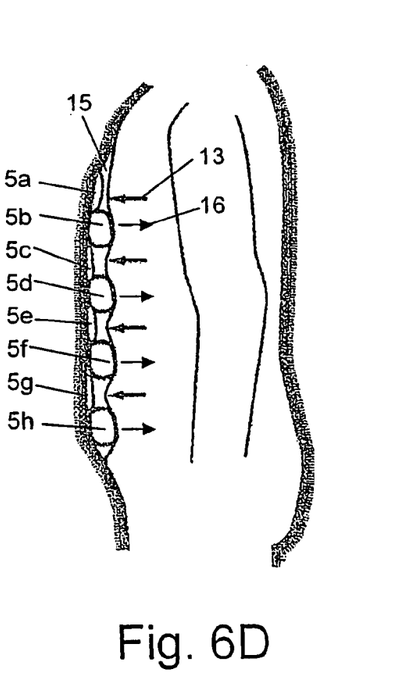
FIG. 6D shows a cross section through FIG. 6B.

As can be seen in FIGS. 6C and 6D, each showing cross sections of the operative states of FIG. 6A and FIG. 6B, the switching of each skin stimulation means 5a from the negative pressure state into the overpressure state, and vice versa, effects a corresponding change in the stimulation areas 13, 16. This leads to a massage of the fatty tissue in the hypodermis.

Figure 7A:
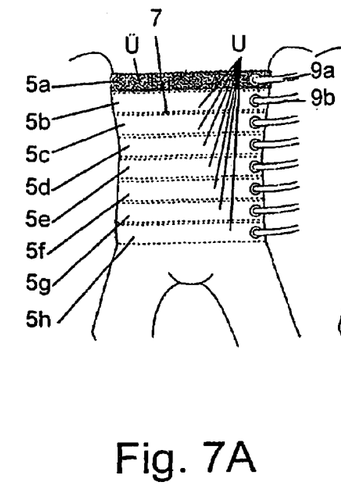
FIG. 7A shows the embodiment of FIG. 6A in a further operative state.
Figure 7B:
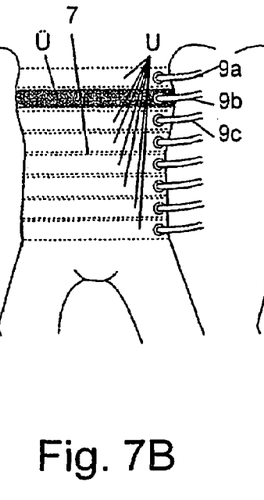
FIG. 7B shows the embodiment of FIG. 7A in a further operative state.
Figure 7C:
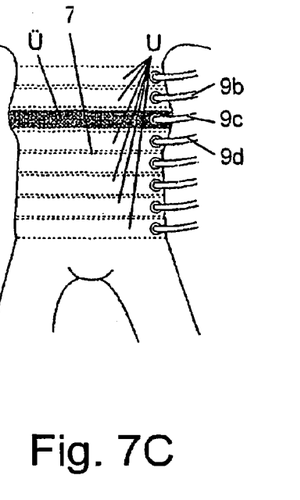
FIG. 7C shows the embodiment of FIG. 7A in a further operative state.

A further example of controlling the stimulation area of the fitness device according to the invention is shown in FIGS. 7A to 7F. The same fitness device is used as shown in FIGS. 6A to 6D. FIGS. 7A to 7C show a front view, and each of FIGS. 7D to 7F a cross section through the front view shown thereabove.

In FIGS. 7A to 7F, each of the skin stimulation means 5a-h can be controlled separately and independently of the remaining skin stimulation means. It is thereby possible to generate a stimulation area which moves over the body surface through a selective and coordinated actuation of the skin stimulation means.

For instance, in FIG. 7A the uppermost skin stimulation means 5a is first acted upon by overpressure while the remaining skin stimulation means 5b-h are acted upon by negative pressure. The pressure in the uppermost skin stimulation means 5a will then be reduced gradually and pressure in the neighboring skin stimulation means 5b positioned thereunder will be built up until the operative state shown in FIG. 7B is reached.

In the operative state of FIG. 7B, the uppermost skin stimulation means 5a is acted upon by negative pressure and the skin stimulation means positioned thereunder by overpressure; the remaining skin stimulation means 5c-h remain unchanged in comparison with the state shown in FIG. 7A.

The above process will now be repeated with the skin stimulation means respectively positioned thereunder until the stimulation area acted upon by overpressure has moved along the fitness device 1 from top to bottom, as shown by the blackened skin stimulation means in FIGS. 7A to 7C. In a next step, pressure will be reduced gradually in the second skin stimulation means 5b and pressure will be built up in the neighboring skin stimulation means 5c positioned thereunder until the state shown in FIG. 7C is reached and overpressure prevails in the third skin stimulation means 5c while the remaining skin stimulation means 5a-b, d-h are acted upon by negative pressure.

In a variant of this method, several stimulation areas can also travel along the body simultaneously, for instance in that in the initial position of FIG. 7A the fifth skin stimulation means 5e from above is additionally acted upon by overpressure and the stimulation area is moved downwards in addition to and in synchronism with the stimulation area of the uppermost skin stimulation means 5a.

Figures 7D, 7E:
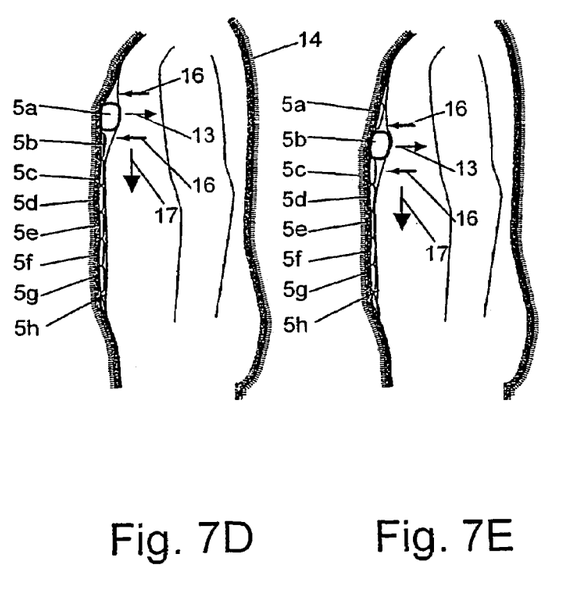
FIG. 7D shows a cross section through the operative state of FIG. 7A.
FIG. 7E shows a cross section through the operative state of FIG. 7B.
Figure 7F:
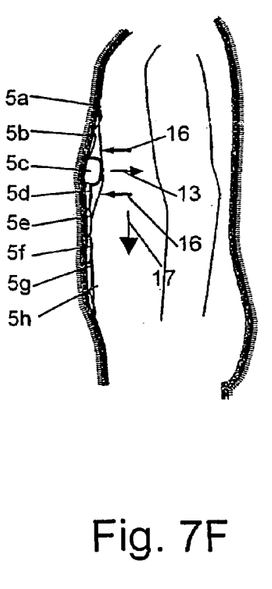
FIG. 7F shows a cross section through the operative state of FIG. 7C.

The movement of the stimulation area by coordinated actuation of the skin stimulation areas 5a to 5h becomes apparent from the cross sections of FIGS. 7D to 7F. Due to the sequence shown in FIGS. 7A to 7C, a stimulation area which includes an overpressure area 13 and two negative pressure areas 16 adjoining said overpressure area 13 at the top and bottom travels in the direction of arrow 17 downwards. This permits a massage-like action on the skin surface, the effect of which also extends into lower layers up into the muscle area.

The movement of the stimulation areas 13 and 16, which in FIGS. 7A to 7F extends downwards, can be reversed by simply changing the actuating operation. To this end, instead of the uppermost skin stimulation means 5a, the lowermost skin stimulation means 5h has just to be started from.

Figures 8A, 8B:
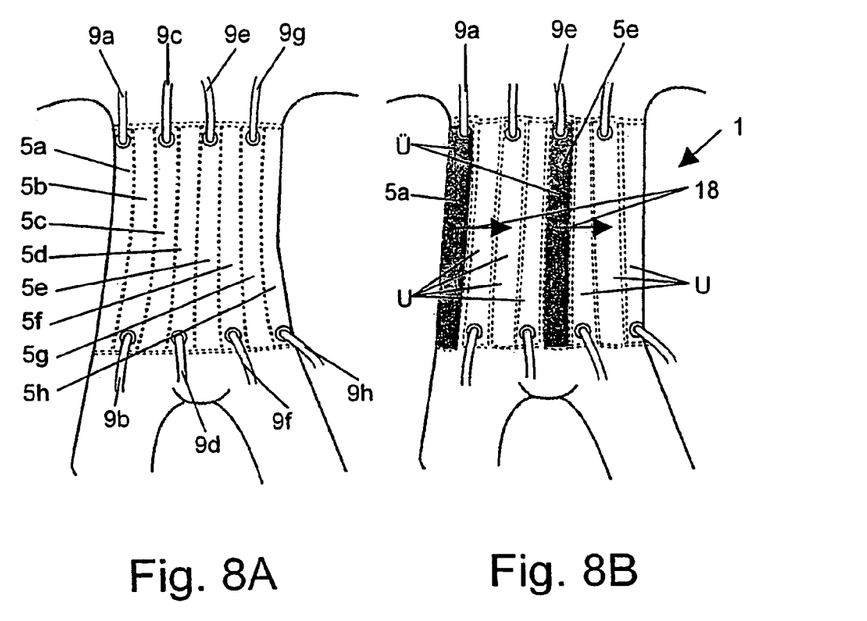
FIG. 8A shows a seventh embodiment of the fitness device according to the invention in a first operative mode.
FIG. 8B shows the embodiment of FIG. 8A in a second operative mode.

FIGS. 8A and 8B show a seventh embodiment of the fitness device of the invention in which, in contrast to the embodiment of FIGS. 5, 6 and 7, the skin stimulation means 5a-h and thus the stimulation areas assigned to said skin stimulation means do not extend in circumferential direction, but extend in the longitudinal direction of the body.

A movement of the stimulation area in circumferential direction is possible through selective actuation of the skin stimulation means 5a-h of the embodiment of FIGS. 8A and 8 D when the individual skin stimulation means 5 are actuated in a way similar to the one in the embodiment of FIGS. 7A to 7F.

This is shown by way of example in FIG. 8B, where it is shown that two stimulation areas Ü acted upon by overpressure move in the circumferential direction of the body in the direction of arrow 18. Except for the different direction of movement 18 (in circumferential direction instead of direction 17, which is oriented downwards), the functional sequence of the mode of operation shown in FIG. 8B corresponds to the one shown in FIGS. 7A-7F, so that reference can here be made to the description of FIGS. 7A-7F.

Figure 9:
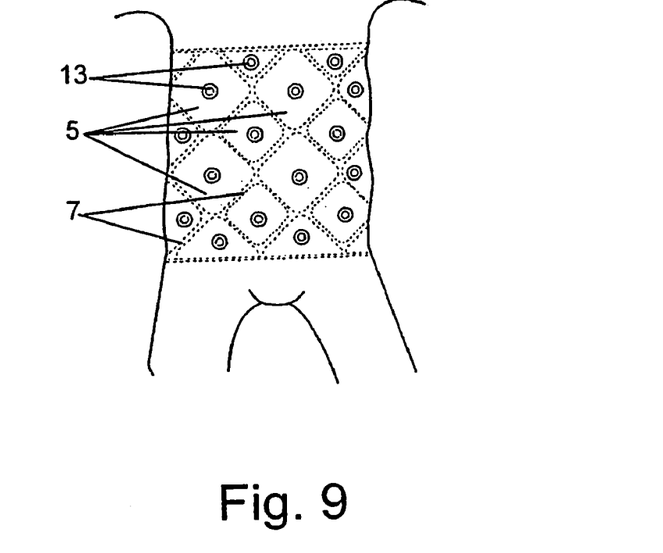
FIG. 9 shows an eighth embodiment of the fitness device according to the invention.

FIG. 9 shows an eighth embodiment of the fitness device of the invention, wherein the skin stimulation means 5 are configured in the form of independently actuable small polygonal areas. The greater the number of skin stimulation means is and the smaller their size, the more selectively can the stimulation areas be composed of the coordinated simultaneous actuation of several skin stimulation means and moved over the body surface.

In this instance, too, the procedural sequence is the same as described in the embodiment shown in FIGS. 7A to 7F. For the movement of a stimulation area around the body, and starting from a skin stimulation means 5 or a group of skin stimulation means 5 acted upon by overpressure, an overpressure is built up in an environment of said skin stimulation means which is positioned in the intended direction of movement, while the pressure in the skin stimulation means originally acted upon by overpressure is reduced. This process is continued so that the overpressure area will move in a specific direction over the body.

Instead of the movement of a stimulation area acted upon by overpressure, as has so far been described, a stimulation area acted upon by negative pressure can also be moved over the body. In this case, all of the skin stimulation means 5 of a fitness device are initially acted upon by overpressure; only one skin stimulation means or a group thereof is acted upon by negative pressure. Starting from said negative pressure region, neighboring skin stimulation means that are within the intended direction of movement of the stimulation area are acted upon by negative pressure.

Figure 10:
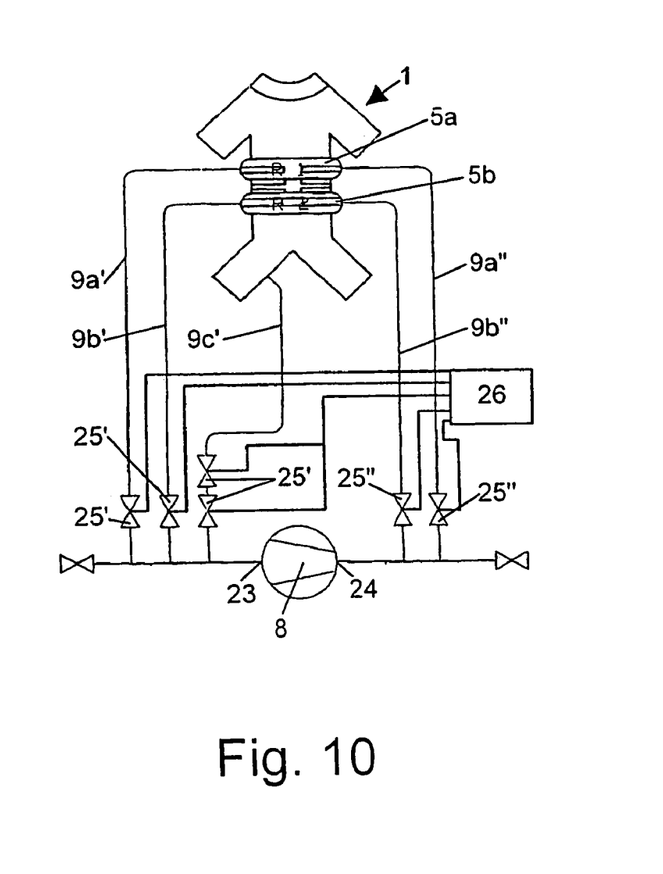
FIG. 10 shows a ninth embodiment of the fitness device according to the invention.

FIG. 10 schematically shows the fluidic structure of a fitness device 1 by way of example.

The pump device 8 generates a negative pressure at a suction side 23 and an overpressure at the pressure side 24.

The suction side 23 or the pressure side 24, respectively, is connected to a skin stimulation means 5 and 6, respectively, via valves 25', 25" that are actuated by control means 26.

When the valves 25' at the suction side are opened and the valves 25" at the pressure side are closed, the skin stimulation means 5 will be acted upon by negative pressure. When valves 25' are closed and valves 25" are opened, the skin stimulation means 5 will be acted upon by overpressure.

In the embodiment of FIG. 10, each skin stimulation means 5 is provided with a line 9' at the suction side and a line 9" at the pressure side. Alternatively, instead of the one-way valves 25, three-way valves (not shown) could also be used, the two input ports thereof being connected to the pressure side and the suction side, and the output side thereof to the skin stimulation means. When three-way valves are used, only one single line to each skin stimulation means is needed, and depending on the switching position of the three-way valve, the skin stimulation means can then be acted upon via said line with both overpressure and negative pressure.

Figure 11A:
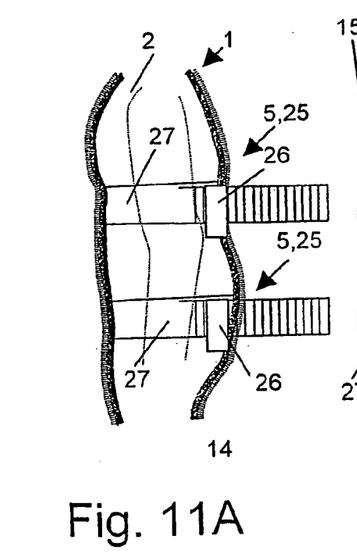
FIG. 11A shows a tenth embodiment of the fitness device according to the invention in a first operative position in cross section.
Figure 11B:
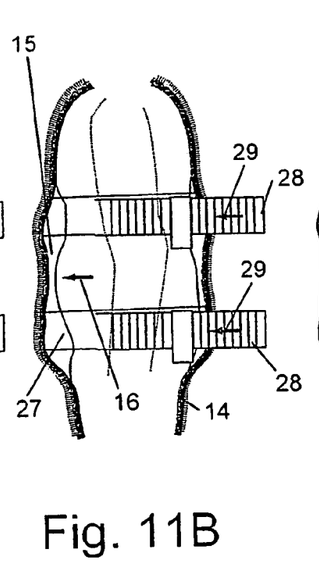
FIG. 11B shows the embodiment of FIG. 11A in a second operative position in cross section.
Figure 11C:
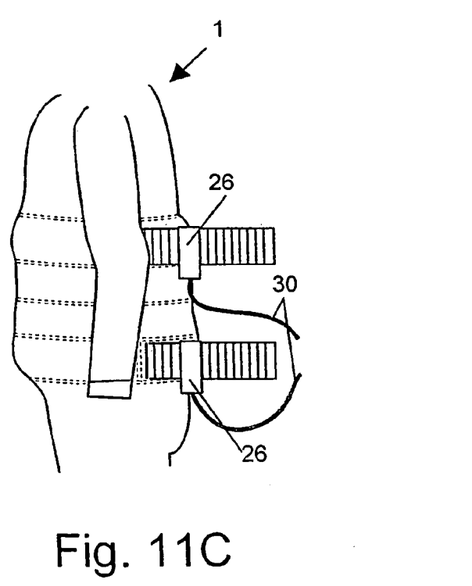
FIG. 11C shows the operative position of FIG. 11B in a side view.

FIGS. 11A to 11C show a last embodiment of a fitness device 1 according to the invention.

Instead of a fluidic pump device 8, the fitness device comprises mechanical elements as skin stimulation means 5 by which the overpressure state is adjusted in a purely mechanical way without fluid pressure. This is achieved by a belt-like design.

Each of the belt devices 5 comprises a motor 26 and a belt 27. The belt 27 encloses the body 2 of the wearer at least in part and can be adjusted in its circumference.

The cover 14 of the fitness device 1 encloses the wearer's body in an air-tight manner. When the circumference of the belt devices 25 is now enlarged by actuation of the motors 26 in that a loose end 28 of the belt 27 is moved in the direction of arrows 29, a hollow chamber 15 that is acted upon with negative pressure is formed due to the enlarged circumference inside the fitness device 1. To achieve such a condition, the belts 27 must have an adequate strength. A negative pressure zone 16 is thereby created, as shown in FIG. 11B.

As shown in the side view of FIG. 11C, which corresponds to the cross-sectional view of FIG. 11B, energy supply lines 30 are provided for the motors 26.

By contracting the belts 27, i.e. movement opposite to the direction of arrows 29 of FIG. 11B, the skin stimulation means 5 is transferred into the overpressure state in that pressure is exerted by the belts 27 on the skin in the stimulation area.

The invention claimed is:

1. A fitness device in the form of a garment, comprising:
a plurality of skin stimulation means to act on the skin of a wearer of the fitness device in a stimulation area;
said plurality skin stimulation means each having at least one pressure chamber configured as a hollow chamber;
a source of negative pressure and overpressure communicating with each said skin stimulation means;
a controller associated with said source of negative pressure and overpressure for coordinating a sequence of switching of the individual skin stimulation means negative pressure state into an overpressure state
a said hollow chamber producing a negative pressure acting on a skin surface of said skin in said stimulation area during said negative pressure state;
a said hollow chamber being supported on said skin surface during said overpressure state and generating an overpressure on said skin surface; and
wherein the skin stimulation means further comprises an elastic element by which in the overpressure state pressure is exerted on the stimulation area.

2. The fitness device according to claim 1, wherein there are a plurality of said skin stimulation means that can be transferred independently of one another from the negative pressure state into the overpressure state.

3. The fitness device according to claim 1 wherein the skin stimulation means comprises a pressure chamber which in the overpressure state is acted upon with a chamber pressure greater than ambient pressure.

4. The fitness device according to claim 1 wherein the skin stimulation means is supported on the skin surface in the overpressure state.

5. The fitness device according to claim 1 wherein when in the negative pressure state the skin stimulation means is spaced apart from the skin surface.

6. The fitness device according to claim 1 wherein the hollow chamber comprises a flexible cover at least in sections.

7. The fitness device according to claim 1 and further comprising a climate control means for controlling the temperature of the fluid passed into the fitness device.

8. The fitness device according to claim 1 wherein the fitness device comprises a flexible cover which is fluid-impermeable in the stimulation area.

9. The fitness device according to claim 1 wherein said garment is of a flexible material that permits the wearer to move the part of the body on which said garment is placed.

10. A fitness device in the form of a garment, comprising:
a plurality of skin stimulation means to act on the skin of a wearer of the fitness device in a stimulation area;
said plurality skin stimulation means each having at least one pressure chamber configured as a hollow chamber;
a source of negative pressure and overpressure communicating with each said skin stimulation means;
a controller associated with said source of negative pressure and overpressure for coordinating a sequence of switching of the individual skin stimulation means negative pressure state into an overpressure state
a said hollow chamber producing a negative pressure acting on a skin surface of said skin in said stimulation area during said negative pressure state;
a said hollow chamber being supported on said skin surface during said overpressure state and generating an overpressure on said skin surface; and
wherein the skin stimulation means further comprises an element by which in the overpressure state mechanical pressure can be produced to act on the body of wearer.

11. The fitness device according to claim 10, wherein the element comprises a belt-like member whose circumference is variable and which encloses at least a part of the body of the wearer.

12. A fitness device in the form of a garment, comprising:
a plurality of skin stimulation means to act on the skin of a wearer of the fitness device in a stimulation area;
said plurality skin stimulation means each having at least one pressure chamber configured as a hollow chamber;
a source of negative pressure and overpressure communicating with each said skin stimulation means;
a controller associated with said source of negative pressure and overpressure for coordinating a sequence of switching of the individual skin stimulation means negative pressure state into an overpressure state
a said hollow chamber producing a negative pressure acting on a skin surface of said skin in said stimulation area during said negative pressure state;
a said hollow chamber being supported on said skin surface during said overpressure state and generating an overpressure on said skin surface;
and further comprising at least one magnetic field means for producing a magnetic field acting on the body of the wearer of the fitness device.

13. The fitness device according to claim 12 and further comprising a climate control means for controlling the moisture of the fluid passed into the fitness device.

14. The fitness garment according to claim 12 wherein said garment is of a flexible material that permits the wearer to move the part of the body on which said garment is placed.

15. A slimming method by means of a fitness device which is designed as a garment, comprising the steps of:
providing said garment with a plurality of fluid pressure-actuated skin stimulation means to contact an area of the skin of a user, each said stimulation means having at least one hollow chamber;
independently operating each of said plurality of stimulation means to alternatingly apply a negative pressure and an overpressure to a stimulation area of the wearer's skin surface by alternatingly provide a negative pressure and an overpressure in said at least one hollow chamber; and
at the same time providing said negative pressure to said at least one hollow chamber of at least a first skin stimulation means of said plurality of skin stimulation means and said overpressure to said at least one hollow chamber of at least a second skin stimulation means of said plurality of skin stimulation means.

16. The method according to clam 15, further comprising the step of:
providing a plurality of said skin stimulation means; and
switching the operation of said plurality of skin stimulation means from the overpressure state into the negative pressure state to cause the stimulation area to move in a predetermined direction over the skin surface.

17. The method of slimming according to claim 15 wherein the garment of said fitness device is of a flexible material that permits the wearer to move the part of the body on which said garment is placed.

* * * * *